(12) United States Patent
Zhou et al.

(10) Patent No.: US 10,273,253 B1
(45) Date of Patent: Apr. 30, 2019

(54) METHOD FOR PRODUCING AN IONIC LIQUID

(71) Applicant: PPG Industries Ohio, Inc., Cleveland, OH (US)

(72) Inventors: Hongying Zhou, Allison Park, PA (US); Shanti Swarup, Allison Park, PA (US); Justin M. Jones, Cranberry Township, PA (US); Steven E. Bowles, Pittsburgh, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 15/728,529

(22) Filed: Oct. 10, 2017

(51) Int. Cl.
*C07F 7/18* (2006.01)

(52) U.S. Cl.
CPC .......... *C07F 7/1892* (2013.01); *C07F 7/1804* (2013.01)

(58) Field of Classification Search
CPC .................................................... C07F 7/1892
See application file for complete search history.

(56) References Cited

U.S. PATENT DOCUMENTS

| | | | |
|---|---|---|---|
| 4,148,772 A | 4/1979 | Marchetti et al. |
| 4,468,307 A | 8/1984 | Wismer et al. |
| 4,793,867 A | 12/1988 | Charles et al. |
| 4,931,157 A | 6/1990 | Valko et al. |
| 5,275,645 A | 1/1994 | Ternoir et al. |
| 5,588,989 A | 12/1996 | Vonk et al. |
| 5,618,860 A | 4/1997 | Maurer et al. |
| 7,122,599 B2 | 10/2006 | Haubennestel et al. |
| 7,749,368 B2 | 7/2010 | McMurdie et al. |
| 7,842,762 B2 | 11/2010 | Zawacky et al. |
| 8,187,489 B1 | 5/2012 | Davis |
| 8,673,091 B2 | 3/2014 | McMillen et al. |
| 9,090,797 B2 | 7/2015 | Tang et al. |
| 2007/0043234 A1 | 2/2007 | Vaultier et al. |
| 2009/0030158 A1 | 1/2009 | Amano et al. |
| 2010/0196724 A1 | 8/2010 | Yamasaki et al. |
| 2013/0344253 A1 | 12/2013 | Abrami et al. |

FOREIGN PATENT DOCUMENTS

| | | |
|---|---|---|
| CN | 101397307 A | 4/2009 |
| CN | 103614118 A | 3/2014 |
| CN | 103709995 A | 4/2014 |
| WO | 2014116221 A1 | 7/2014 |
| WO | 2015094917 A1 | 6/2015 |

OTHER PUBLICATIONS

Chernyy et al., "Superhydrophilic Polyelectrolyte Brush Layers with Imparted Anti-Icing Properties: Effect of Counter ions", American Chemical Society, Applied Materials & Interfaces, 2014, 6, pp. 6487-6496.

*Primary Examiner* — Golam M Shameem
(74) *Attorney, Agent, or Firm* — Alicia M. Passerio, Esq.

(57) ABSTRACT

The present invention is directed to a method of preparing an alkoxy silane functional ionic liquid comprising reacting a halogenated compound comprising a halogen and an active hydrogen functional group, an isocyanato functional alkoxy silane, and an ionizable compound capable forming an ionic bond with the halogen to form the alkoxy silane functional ionic liquid. The present invention is also directed to alkoxy silane functional ionic liquids.

11 Claims, No Drawings

METHOD FOR PRODUCING AN IONIC LIQUID

FIELD OF THE INVENTION

The present invention is directed towards methods for producing ionic liquids, and the ionic liquids produced therefrom.

BACKGROUND INFORMATION

Ionic liquids are salts having relatively low melting points. Some ionic liquids may be liquid at ambient temperature or less. They may also be referred to as liquid electrolytes, ionic melts, ionic fluids, fused salts, liquid salts, or ionic glasses.

Ionic liquids are of interest because of their many potential applications. Ionic liquids have proven to be effective solvents and useful electrolyte materials because of their electrical conductance. They have also been utilized for their catalytic activity, among other uses.

Current methods of producing ionic liquids have proven to be synthetically complicated and expensive resulting in a high-cost for ionic liquids.

It would be desirable to provide a method of preparing an ionic liquid that is synthetically simple and inexpensive.

SUMMARY OF THE INVENTION

Disclosed herein is a method of preparing an alkoxy silane functional ionic liquid comprising: reacting a halogenated compound comprising a halogen and an active hydrogen functional group, an isocyanato functional alkoxy silane, and an ionizable compound capable forming an ionic bond with the halogen to form the alkoxy silane functional ionic liquid.

Also disclosed herein are alkoxy silane functional ionic liquids.

DETAILED DESCRIPTION OF THE INVENTION

The present invention is directed towards a method of preparing an alkoxy silane functional ionic liquid comprising reacting a halogenated compound comprising a halogen and an active hydrogen functional group, an isocyanato functional alkoxy silane, and an ionizable compound capable forming an ionic bond with the halogen to form the alkoxy silane functional ionic liquid.

Ionic liquids are salts that are liquid at temperatures less than or equal to 400° C., such as at temperatures less than 100° C., such as at temperatures less than or equal to 75° C., such as at temperatures less than or equal to room temperature (i.e., 25° C.) at atmospheric pressure (101,325 Pa). Ionic liquids comprise a cation and an anion. Suitable cations may include, for example, imidazolium; pyridinium; pyrrolidinium; phosphonium; ammonium; guanidinium; isouronium; thiouronium; and sulphonium groups. Suitable anions may include, for example, a halide such as fluoride, chloride, bromide and iodide; tetrafluoroborate; hexafluorophosphate; bis(trifluoromethylsulfonyl)imide; tris(pentafluoroethyl)trifluorophosphate (FAPs); trifluoromethanesulfonate; trifluoroacetate; methylsulfate; octylsulfate; thiocyanate; organoborate; and p-toluenesulfonate. The ionic liquid may comprise any combination of the above cation(s) and anion(s), and other suitable cations or anions not listed may be used.

The halogenated compound comprises a compound comprising at least one halogen atom substituent and at least one active hydrogen functional group. As used herein, the term "halogen" or "halogen atom" refers to elements included in IUPAC group 17 of the periodic table of the elements and includes, for example, fluorine, chlorine, bromine and iodine. As used herein, the term "active hydrogen functional group(s)" refers to those groups that are reactive with isocyanates as determined by the Zerewitnoff test as is described in the JOURNAL OF THE AMERICAN CHEMICAL SOCIETY, Vol. 49, page 3181 (1927) and may include hydroxyl groups, primary amine groups, secondary amine groups, thiol groups, and combinations thereof.

The halogenated compound may comprise a halogenated alcohol. The halogenated alcohol comprises an alcohol having at least one halogen substituent in a pendant or terminal position. The alcohol may comprise a linear or branched $C_1$ to $C_{12}$ alkyl chain having a hydroxyl functional group in a pendant or terminal position. The alcohol may comprise ethanol, propanol, butanol, isobutanol, pentanol, hexanol, septanol, octanol, nonanol, decanol, undecanol, or dodecanol. The halogen may comprise fluorine, chlorine, bromine, iodine, or combinations thereof. Non-limiting examples of suitable halogenated alcohols include 2-chloroethanol, 3-chloro-1-propanol, 4-chloro-1-butanol, 3-chloro-1-butanol, 5-chloro-1-pentanol, 6-chloro-1-hexanol, and the like, as well as combinations thereof.

The halogenated compound may comprise a halogenated polymeric compound comprising a halogen and an active hydrogen functional group, which optionally may comprise more than one halogen and active hydrogen functional group per molecule. The halogenated polymeric compound may comprise, for example, the reaction product of an epoxy-functional polymeric compound and a halogenated acid, alcohol, amine or thiol, the reaction of which results in a halogenated polymeric compound comprising a halogen and a hydroxyl functional group resulting from the ring-opening reaction of the epoxide functional group. The epoxy-functional polymeric compound may comprise, for example, 1 to 6 epoxide functional groups. The epoxy-functional polymeric compound may comprise a mono- or poly-glycidyl ether of a substituted or unsubstituted $C_1$ to $C_{36}$ alkane group; a mono- or poly-glycidyl ether of a substituted or unsubstituted $C_6$ to $C_{36}$ aromatic group; a mono- or poly-glycidyl ether of a substituted or unsubstituted $C_3$ to $C_{36}$ cycloaliphatic group; a mono- or poly-glycidyl ether of a polyester having a number average molecular weight ($M_n$) of greater than 150 g/mol; a mono- or poly-glycidyl ether of a polyether having a number average molecular weight ($M_n$) of greater than 200 g/mol; a mono- or poly-glycidyl ether of a polyurethane having a number average molecular weight ($M_n$) of greater than 500 g/mol; or a mono- or poly-glycidyl ether of an acrylic resin having a number average molecular weight ($M_n$) of greater than 1,000 g/mol. The halogenated acid may comprise a carboxyl-functional substituted or unsubstituted $C_1$ to $C_{36}$ alkanediyl or $C_6$ to $C_{36}$ divalent aromatic group that further comprises a halogen substituent. In terms of the present invention, a divalent aromatic group may be, for example, a substituted or unsubstituted divalent benzene group. The halogenated alcohol may comprise a hydroxyl-functional substituted or unsubstituted $C_1$ to $C_{36}$ alkanediyl or $C_6$ to $C_{36}$ divalent aromatic group that further comprises a halogen substituent. The halogenated amine may comprise an amino-functional substituted or unsubstituted $C_1$ to $C_{36}$ alkanediyl or $C_6$ to $C_{36}$ divalent aromatic group that further comprises a halogen substituent. The halogenated thiol may comprise a thiol-functional substituted or unsubstituted $C_1$ to $C_{36}$ alkanediyl or $C_6$ to $C_{36}$ divalent aromatic group that further comprises a halogen substituent. The halogen substituent may comprise fluorine, chlorine, bromine, iodine, or combinations thereof. The halogenated polymeric compound comprising the reaction product of the epoxy-functional polymeric compound and the halogenated acid may comprise a hydroxyl group, an ether group, an ester group, and a halogen substituent, for each epoxide group of the epoxy-functional compound that undergoes a ring-opening reaction with an acid group of a halogenated acid.

The isocyanato functional alkoxy silane may comprise an isocyanato functional monoalkoxy silane, dialkoxy silane or trialkoxy silane. For example, the isocyanato functional alkoxy silane may comprise an isocyanato functional trialkoxy silane according to the following Formula (I):

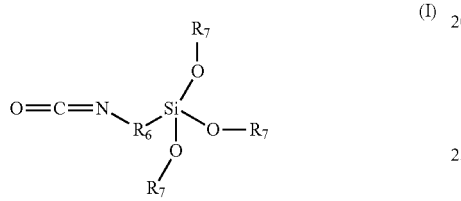

wherein $R_6$ is an alkanediyl group, and $R_7$ is a $C_1$ to $C_4$ alkyl group. The alkanediyl group, $R_6$, may comprise a linear or branched $C_1$ to $C_{36}$ alkanediyl group, a linear or branched $C_3$ to $C_{36}$ cycloaliphatic group, or a linear or branched $C_6$ to $C_{36}$ aromatic group. The $C_1$ to $C_4$ alkyl group, $R_7$, each independently form an alkoxy group with the oxygen atom they are attached to, such as, for example, methoxy, ethoxy, propoxy, isopropoxy, butoxy, or combinations thereof. Non-limiting examples of the isocyanato functional alkoxy silane may include, without limitation, isocyanatopropyl trimethoxy silane, isocyanatobutyl trimethoxy silane, isocyanatopentyl trimethoxy silane, isocyanatohexyl trimethoxy silane, and the like.

The ionizable compound capable forming an ionic bond with the halogen may comprise a compound comprising at least one heteroatom, such as nitrogen, phosphorus and/or sulfur, such as, for example, imidazole, pyridine, pyrrolidine, phosphine, ammonia, guanidine, urea, thiourea or thioether. Such compounds may be substituted or unsubstituted. Non-limiting examples of suitable imidazole compounds include N-methyl imidazole, 1-ethyl imidazole, 2-ethyl imidazole, 2,4,5-triphenyl imidazole, and the like.

The various reactions and reaction steps described herein may be performed in the presence of a catalyst. The catalyst may comprise a metal catalyst, such as a tin catalyst. Non-limiting examples of suitable tin catalysts include dibutyltin oxide, dibutyltin octoate, dibutyltin dilaurate, and the like.

According to the present invention, the method may comprise a first step comprising reacting the halogenated compound and the isocyanato functional alkoxy silane to form a halogenated alkoxy silane, and a second step comprising reacting the halogenated alkoxy silane with the ionizable compound to form the alkoxy silane functional ionic liquid. During the second step of the method, the ionizable compound substitutes the halogen group of the halogenated alkoxy silane to form a compound comprising a cationic group, such as, for example, imidazolium; pyridinium; pyrrolidinium; phosphonium; ammonium; guanidinium; isouronium; thiouronium; or sulphonium, and a halogen anion (i.e., halide) is generated, such as, for example, fluoride, chloride, bromide or iodide. The cationic group may form an ionic bond with the halide to form the ionic liquid. Non-limiting examples of the first and second steps are provided below in Scheme 1 and Scheme 2, and the first and second steps are discussed below and provided in Scheme 1-A and Scheme 1-B, and Scheme 2-A and Scheme 2-B.

Scheme 1 illustrates the two-step formation of a monomeric ionic liquid according to the present invention.

Scheme 1

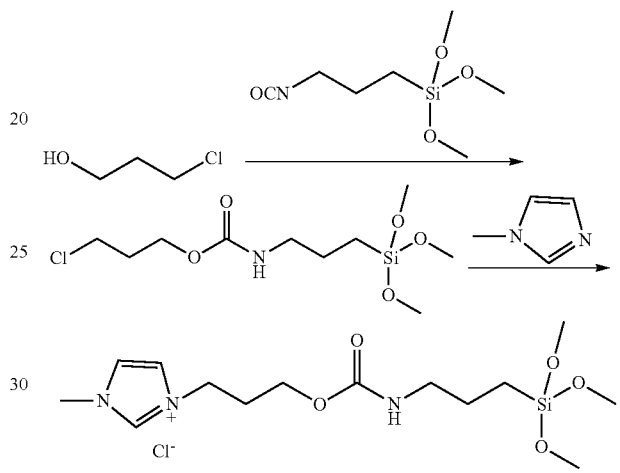

A non-limiting example of the first step comprising the reaction of a halogenated compound and an isocyanato functional alkoxy silane to form a reaction product comprising a halogenated alkoxy silane is provided below in Scheme 1-A. As shown in Scheme 1-A, 3-chloro-propanol reacts with isocyanatopropyl trimethoxy silane to form a reaction product comprising a chlorinated urethane trimethoxy silane.

Scheme 1-A

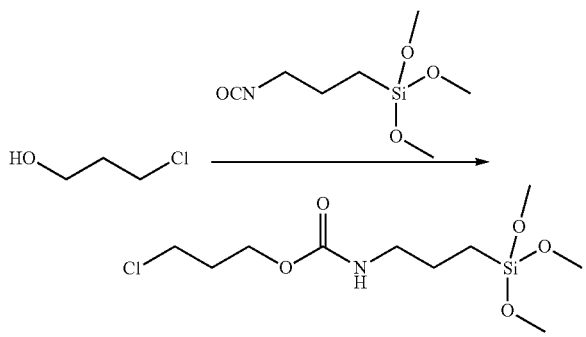

A non-limiting example of the reaction of the second step comprising reacting the halogenated alkoxy silane with the ionizable compound to form the alkoxy silane functional ionic liquid is provided below in Scheme 1-B. A halogenated trimethoxy silane is reacted with N-methyl imidazole to form a trimethoxy silane functional ionic liquid.

Scheme 1-B

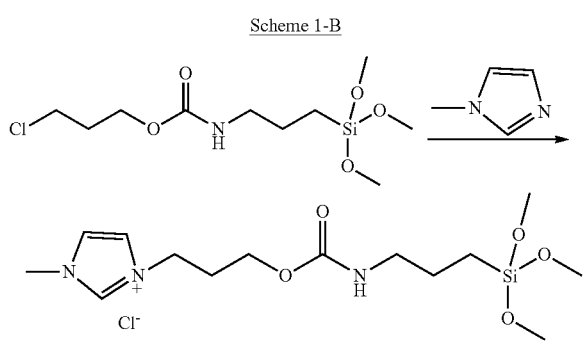

Scheme 2 illustrates the formation of a monomeric or polymeric ionic liquid according to the present invention wherein the halogenated compound is first produced by reacting an epoxy-functional compound with a halogenated acid, wherein n≥1, such as 1 to 6, such as 2 to 6, and R is a monovalent or polyvalent, substituted or unsubstituted $C_1$-$C_{36}$ alkane group, a monovalent or polyvalent $C_6$-$C_{36}$ aromatic group, a monovalent or polyvalent $C_3$-$C_{36}$ cycloaliphatic group, a monovalent or polyvalent polyester group having a number average molecular weight ($M_n$) of greater than 200 g/mol, a monovalent or polyvalent polyether group having a number average molecular weight ($M_n$) of greater than 200 g/mol, a monovalent or polyvalent acrylic resin having a number average molecular weight ($M_n$) of greater than 500 g/mol, or a monovalent or polyvalent polyurethane group having a number average molecular weight ($M_n$) of greater than 500 g/mol.

Scheme 2

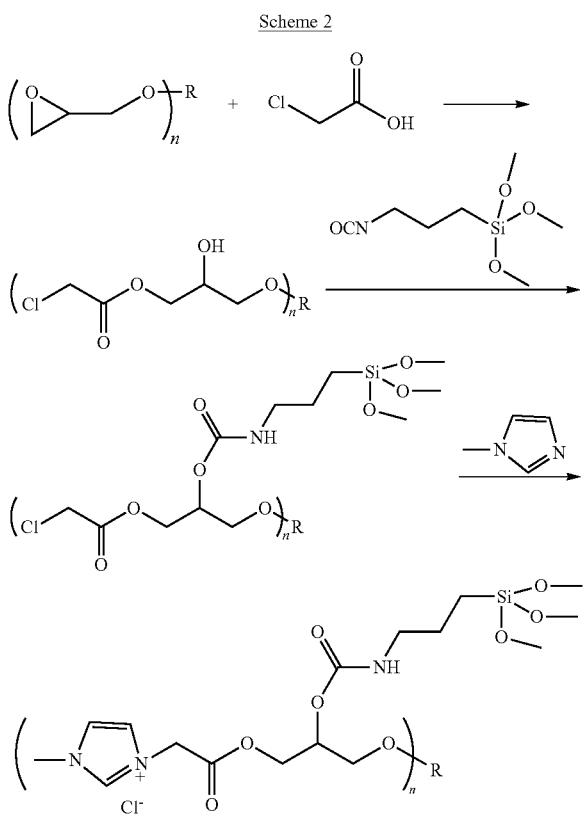

A non-limiting example of the first step comprising the reaction of a halogenated compound and an isocyanato functional alkoxy silane to form a reaction product comprising a halogenated alkoxy silane is provided below in Scheme 2-A. As shown in Scheme 2-A, a monomeric (when n=1) or polymeric (when n≥2, such as 2 to 6) halogenated alcohol is reacted with isocyanatopropyl trimethoxy silane to form a reaction product comprising a monomeric or polymeric chlorinated urethane trimethoxy silane.

Scheme 2-A

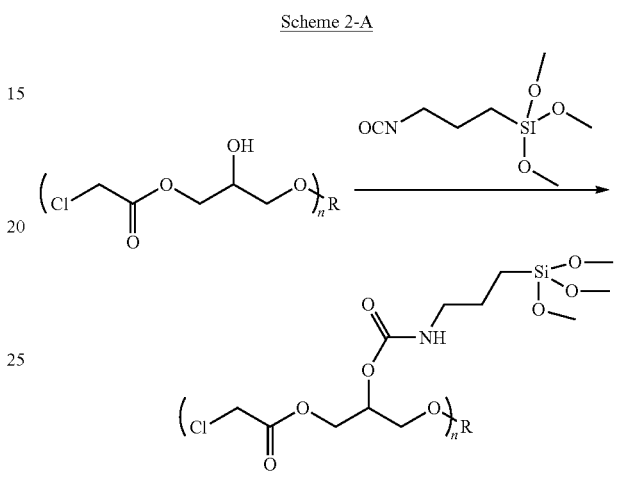

A non-limiting example of the reaction of the second step comprising reacting the halogenated alkoxy silane with the ionizable compound to form the alkoxy silane functional ionic liquid is provided below in Scheme 2-B. A monomeric or polymeric chlorinated urethane trimethoxy silane is reacted with N-methyl imidazole to form a monomeric or polymeric trimethoxy silane functional ionic liquid.

Scheme 2-B

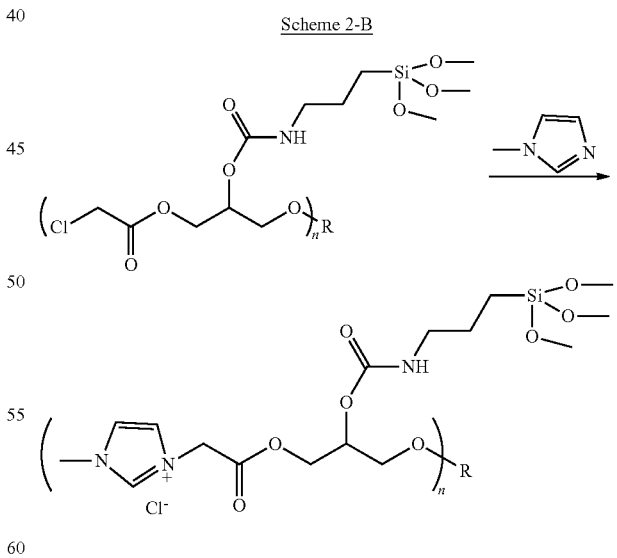

The ratio of isocyanato groups from the isocyanato functional alkoxy silane to active hydrogen functional groups from the halogenated compound present in the first step of the method may be at least 1:3, such as at least 1:2, such as at least 1:1.1, such as at least 1:1, and may be no more than 3:1, such as no more than 1.5:1, such as no more than 1.1:1, such as no more than 1:1. The ratio of isocyanato groups from the isocyanato functional alkoxy silane to active hydrogen functional groups from the halogenated compound present in the first step of the method may be 1:3 to 3:1, such as 1:2 to 1.5:1, such as 1:1.1 to 1.1:1.

The ratio of halogen substituents from the halogenated alkoxy silane to molecules of ionizable compound may be at least 1:3, such as at least 1:2, such as at least 1:1.1, such as at least 1:1, and may be no more than 3:1, such as no more than 1.5:1, such as no more than 1.1:1, such as no more than 1:1. The ratio of halogen substituents from the halogenated alkoxy silane to molecules of the ionizable compound may be 1:3 to 3:1, such as 1:2 to 1.5:1, such as 1:1.1 to 1.1:1.

According to the present invention, the method for making an alkoxy silane functional ionic liquid may begin by combining the halogenated compound and, optionally, an organic solvent and a catalyst and mixing the components in an inert gas atmosphere, e.g., a nitrogen atmosphere. The mixture may be mixed at room temperature or heated to an elevated temperature of 200° C. or less, such as, for example, at least 70° C. At the elevated temperature, the isocyanato functional alkoxy silane may be added dropwise over a period of time such as, for example, 30 minutes. After addition of the isocyanato functional alkoxy silane, the reaction mixture may be held at the elevated temperature for a sufficient period of time to react the halogenated compound and the isocyanato functional alkoxy silane. After that reaction is complete, an ionizable compound may be added dropwise to the reaction mixture over a period of time such as, for example, 10 minutes. After addition, the reaction mixture may be heated to reflux (e.g., 110.6° C. if toluene is the organic solvent), and held for a sufficient period of time to react the halogenated alkoxy silane and the ionizable compound to form the alkoxy silane functional ionic liquid. The reaction mixture may then be cooled to a temperature such as, for example, 80° C. At that temperature, the agitation may be stopped. After a sufficient period of time, such as, for example, 10 minutes, the reaction mixture may separate into a di-phasic mixture including a first phase comprising the ionic liquid and a second phase comprising the solvent and other organic compounds apart from the ionic liquid. The solvent-containing phase may be removed by decanting, and additional solvent may be removed by vacuum distillation using a vacuum pump.

The temperature and period of time for reacting the halogenated compound and the isocyanato functional alkoxy silane may vary, depending upon the scale of the reaction, the exact reaction conditions and the presence or absence of additional ingredients such as, for example, a catalyst, but generally the time period may be determined by analyzing the contents of the reaction mixture by FT-IR spectrometer until the isocyanate peak at 2259 $cm^{-1}$ was no longer detected, indicating that all of the isocyanato functional groups had been consumed and completion of the reaction and formation of the halogenated alkoxy silane. This "sufficient period of time" to form the halogenated alkoxy silane may be, for example, at least 1 hour, such as at least 3 hours, and may be no more than 10 hours, such as no more than 6 hours, and may range from 1 hour to 10 hours, such as 3 hours to 6 hours.

The temperature and period of time for reacting the halogenated alkoxy silane and the ionizable compound may vary, depending upon the scale of the reaction, the exact reaction conditions and the presence or absence of additional ingredients such as, for example, a catalyst, but generally the time period may be determined by analyzing the contents of the reaction mixture by, for example, thin-layer chromatograph (TLC) or gas chromatography (GC) to determine the presence of unreacted ionizable compound. This "sufficient period of time" to form the alkoxy silane functional ionic liquid may be, for example, at least 1 hour, such as at least 4 hours, and may be no more than 20 hours, such as no more than 6 hours, and may range from 1 hour to 20 hours, such as 4 hours to 6 hours.

According to the present invention, the method may comprise a first step comprising reacting the halogenated compound and the ionizable compound to form an ionic liquid comprising an active hydrogen functional group, and a second step comprising reacting the ionic liquid comprising an active hydrogen functional group with the isocyanato functional alkoxy silane to form the alkoxy silane functional ionic liquid. During the first step of the method, the ionizable compound substitutes the halogen group of the halogenated compound to form a compound comprising a cationic group, such as, for example, imidazolium; pyridinium; pyrrolidinium; phosphonium; ammonium; guanidinium; isouronium; thiouronium; or sulphonium, and a halogen anion (i.e., halide) is generated, such as, for example, fluoride, chloride, bromide or iodide. The cationic group may form an ionic bond with the halide to form the ionic liquid comprising an active hydrogen functional group. Non-limiting examples of the first and second steps are provided below in Scheme 3 and Scheme 4, and the individual steps are discussed below and provided in Scheme 3-A and Scheme 3-B, and Scheme 4-A and 4-B.

Scheme 3 illustrates the formation of a monomeric ionic liquid.

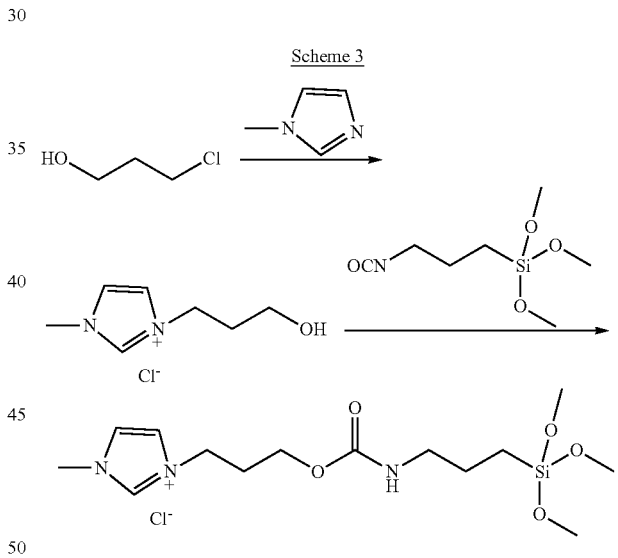

Scheme 3

A non-limiting example of the first step reacting the halogenated compound comprising an active hydrogen functional group and the ionizable compound to form an ionic liquid comprising an active hydrogen functional group is provided below in Scheme 3-A. As shown in Scheme 3-A, 3-chloro-propanol reacts with N-methyl imidazole to form a reaction product comprising an ionic liquid comprising a hydroxyl functional group.

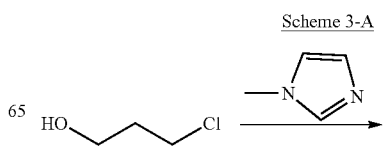

Scheme 3-A

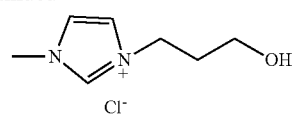

A non-limiting example of the reaction of the second step comprising reacting the ionic liquid comprising an active hydrogen functional group with the isocyanato functional alkoxy silane to form the alkoxy silane functional ionic liquid is provided below in Scheme 3-B. As shown in Scheme 3-B, an ionic liquid comprising a hydroxyl functional group is reacted with isocyanatopropyl trimethoxy silane to form a trimethoxy silane functional ionic liquid.

Scheme 3-B

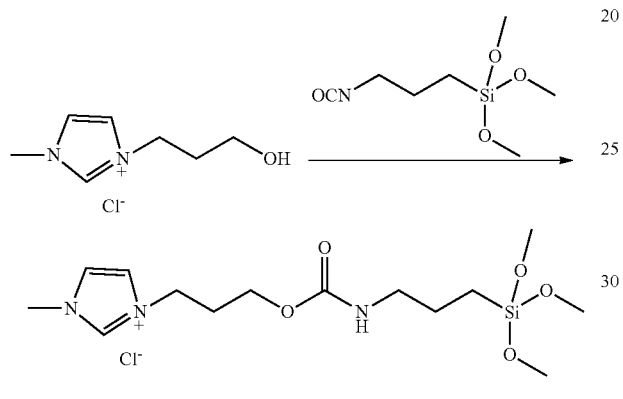

Scheme 4 illustrates the formation of a monomeric or polymeric ionic liquid according to the present invention wherein the halogenated compound is first produced by reacting an epoxy-functional compound with a halogenated acid, wherein $n \geq 1$, such as 1 to 6, such as 2 to 6, and R is a monovalent or polyvalent, substituted or unsubstituted $C_1$-$C_{36}$ alkane group, a monovalent or polyvalent $C_6$-$C_{36}$ aromatic group, a monovalent or polyvalent $C_3$-$C_{36}$ cycloaliphatic group, a monovalent or polyvalent polyester group having a number average molecular weight ($M_n$) of greater than 200 g/mol, a monovalent or polyvalent polyether group having a number average molecular weight ($M_n$) of greater than 200 g/mol, a monovalent or polyvalent acrylic resin having a number average molecular weight ($M_n$) of greater than 500 g/mol, or a monovalent or polyvalent polyurethane group having a number average molecular weight ($M_n$) of greater than 500 g/mol.

Scheme 4

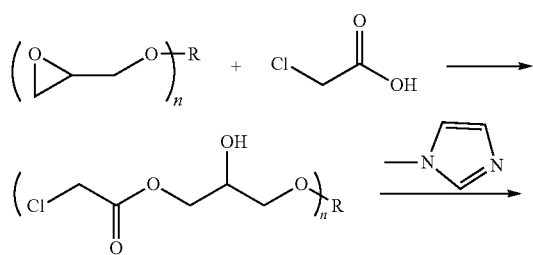

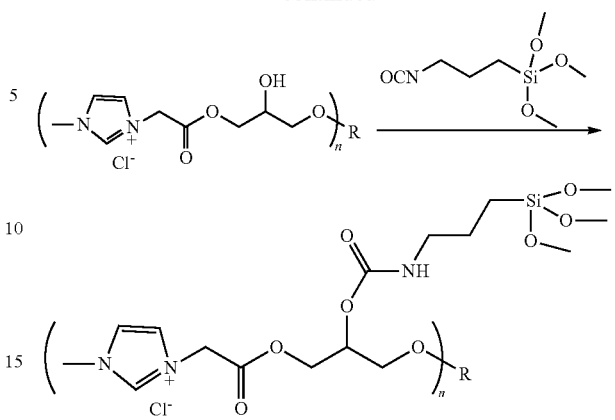

A non-limiting example of the first step reacting the halogenated compound and the ionizable compound to form an ionic liquid comprising an active hydrogen functional group is provided below in Scheme 4-A. As shown in Scheme 4-A, a monomeric (when n=1) or polymeric (when $n \geq 2$, such as 2 to 6) halogenated alcohol is reacted with N-methyl imidazole to form a reaction product comprising a monomeric or polymeric ionic liquid comprising a hydroxyl functional group.

Scheme 4-A

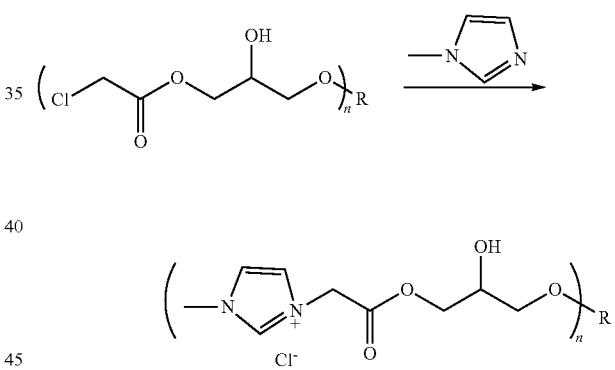

A non-limiting example of the reaction of the second step comprising reacting the ionic liquid comprising an active hydrogen functional group with the isocyanato functional alkoxy silane to form the alkoxy silane functional ionic liquid is provided below in Scheme 4-B. As shown in Scheme 4-B, a monomeric or polymeric ionic liquid comprising a hydroxyl functional group is reacted with isocyanatopropyl trimethoxy silane to form a trimethoxy silane functional ionic liquid.

Scheme 4-B

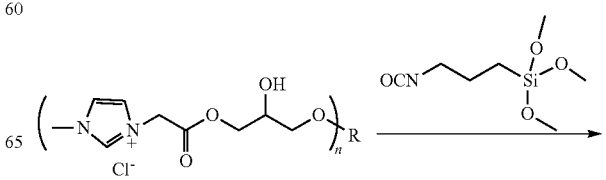

-continued

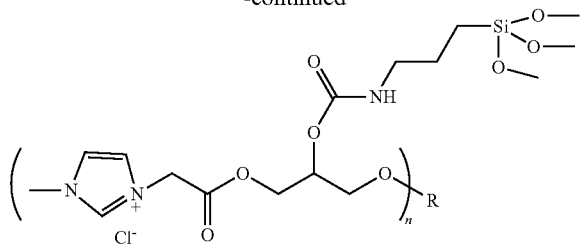

The ratio of halogen substituents from the halogenated compound comprising an active hydrogen functional group to molecules of the ionizable compound may be at least 1:3, such as at least 1:2, such as at least 1:1.1, such as at least 1:1, and may be no more than 3:1, such as no more than 1.5:1, such as no more than 1.1:1, such as no more than 1:1. The ratio of halogen substituents from the halogenated compound comprising an active hydrogen functional group to molecules of the ionizable compound may be 1:3 to 3:1, such as 1:2 to 1.5:1, such as 1:1.1 to 1.1:1.

The ratio of active hydrogen functional groups from the ionic liquid comprising an active hydrogen functional group to isocyanato groups from the isocyanato functional alkoxy silane may be at least 1:3, such as at least 1:2, such as at least 1:1.1, such as at least 1:1, and may be no more than 3:1, such as no more than 1.5:1, such as no more than 1.1:1, such as no more than 1:1. The ratio of active hydrogen functional groups from the ionic liquid comprising an active hydrogen functional group to isocyanato groups from the isocyanato functional alkoxy silane may be 1:3 to 3:1, such as 1:2 to 1.5:1, such as 1:1.1 to 1.1:1.

According to the present invention, the process for making an alkoxy silane functional ionic liquid may begin by combining the halogenated compound comprising an active hydrogen functional group, the ionizable compound, and, optionally, an organic solvent, in an inert gas atmosphere, e.g., a nitrogen atmosphere. The mixture may then be heated to an elevated temperature, such as, for example, the reflux temperature of the organic solvent (e.g., 110.6° C. if toluene is the organic solvent), and held for a sufficient period of time to react the halogenated alcohol and the ionizable compound to form the hydroxyl functional ionic liquid. After that reaction is complete, reaction temperature was cooled to 70° C. A catalyst may optionally be added into the reaction mixture, and the isocyanato functional alkoxy silane may be added dropwise over a period of time such as, for example, 30 minutes. After addition of the isocyanato functional alkoxy silane, the reaction mixture may be held at an elevated temperature for a sufficient period of time to react the hydroxyl functional ionic liquid with the isocyanato functional alkoxy silane and forming the alkoxy silane functional ionic liquid. The reaction mixture may then be cooled to a temperature such as, for example, 80° C. At that temperature, the agitation may be stopped. After a sufficient period of time, such as, for example, 10 minutes, the reaction mixture may separate into a di-phasic mixture including a first phase comprising the ionic liquid and a second phase comprising the solvent and other organic compounds apart from the ionic liquid. The solvent-containing phase may be removed by decanting, and additional solvent may be removed by vacuum distillation using a vacuum pump.

The temperature and period of time for reacting the halogenated compound comprising an active hydrogen functional group, e.g., a halogenated alcohol, and the ionizable compound may vary, depending upon the scale of the reaction, the exact reaction conditions and the presence or absence of additional ingredients such as, for example, a catalyst, but generally the time period may be determined by analyzing the contents of the reaction mixture by thin-layer chromatograph (TLC) or gas chromatography (GC) to determine the presence of unreacted ionizable compound. This "sufficient period of time" to form the ionic liquid comprising an active hydrogen functional group may be, for example, at least 2 hours, such as at least 4 hours, such as at least 8 hours, and may be no more than 24 hours, such as no more than 18 hours, such as no more than 12 hours, and may range from 2 hours to 24 hours, such as 4 hours to 18 hours, such as 8 hours to 12 hours.

The temperature and period of time for reacting the ionic liquid comprising an active hydrogen functional group, e.g., a hydroxyl functional ionic liquid, and the isocyanato functional alkoxy silane may vary, depending upon the scale of the reaction, the exact reaction conditions and the presence or absence of additional ingredients such as, for example, a catalyst, but generally the time period may be determined by analyzing the contents of the reaction mixture by FT-IR spectrometer until the isocyanate peak at 2259 $cm^{-1}$ was no longer detected, indicating that all of the isocyanato functional groups had been consumed and completion of the reaction and formation of the alkoxy silane functional ionic liquid. This "sufficient period of time" to form the halogenated alkoxy silane may be, for example, at least 0.5 hours, such as at least 1 hour, such as at least 3 hours, and may be no more than 24 hours, such as no more than 12 hours, such as no more than 8 hours, and may range from 0.5 hours to 24 hours, such as 1 hour to 12 hours, such as 3 hours to 8 hours.

The present invention is also directed to ionic liquids. The ionic liquids may be produced by the method of the present invention. The ionic liquid may be a monomeric compound having one salt group per molecule. The ionic liquid may be a polymeric compound having at least two salt groups per molecule. Non-limiting examples of ionic liquids of the present invention may be represented by one of the following Formulas (II) to (IV). According to Formula (II) of the present invention, the ionic liquid may comprise a monomeric compound and may comprise or represent:

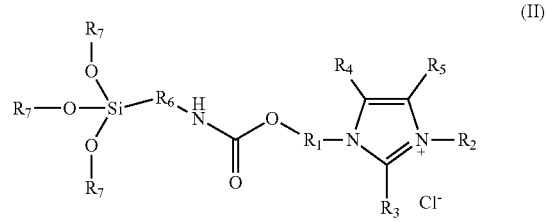

wherein $R_1$ is a substituted or unsubstituted $C_1$-$C_{36}$ alkanediyl group or a substituted or unsubstituted $C_6$-$C_{36}$ divalent aromatic group; $R_2$ is hydrogen, a substituted or unsubstituted $C_1$-$C_{36}$ alkyl group or a substituted or unsubstituted $C_6$-$C_{36}$ aromatic group; $R_3$ is hydrogen or a substituted or unsubstituted $C_1$-$C_{36}$ alkyl group; $R_4$ is hydrogen or a substituted or unsubstituted $C_1$-$C_{36}$ alkyl group; $R_5$ is hydrogen or a substituted or unsubstituted $C_1$-$C_{36}$ alkyl group; $R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is each independently a substituted or unsubstituted $C_1$-$C_4$ alkyl group.

A non-limiting example of a suitable ionic liquid according to Formula (II) include the monomeric compound represented by Formula (III):

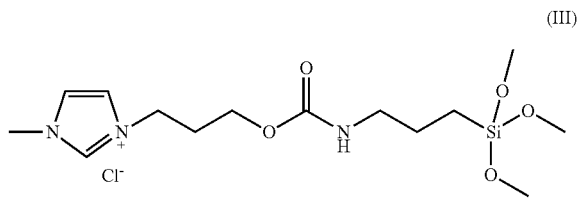

According to Formula (IV) of the present invention, the ionic liquid may comprise a polymeric compound and may comprise or represent:

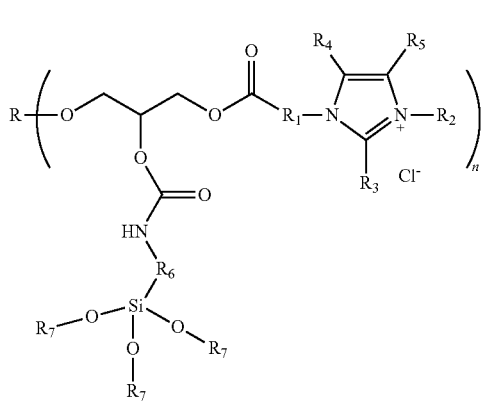

wherein n≥1, such as 1 to 6, such as 2 to 6; R is a monovalent or polyvalent, substituted or unsubstituted $C_1$-$C_{36}$ alkane group, a monovalent or polyvalent $C_6$-$C_{36}$ aromatic group, a monovalent or polyvalent $C_3$-$C_{36}$ cycloaliphatic group, a monovalent or polyvalent polyester group having a number average molecular weight ($M_n$) of greater than 200 g/mol, a monovalent or polyvalent of a polyether group having a number average molecular weight ($M_n$) of greater than 200 g/mol, a monovalent or polyvalent acrylic resin having a number average molecular weight ($M_n$) of greater than 500 g/mol, or a monovalent or polyvalent polyurethane group having a number average molecular weight ($M_n$) of greater than 500 g/mol; $R_1$ is a substituted or unsubstituted $C_1$-$C_{36}$ alkanediyl group, or a substituted or unsubstituted $C_6$-$C_{36}$ aromatic group; $R_2$ is hydrogen, a substituted or unsubstituted $C_1$-$C_{36}$ alkyl group, or a substituted or unsubstituted $C_6$-$C_{36}$ aromatic group; $R_3$ is hydrogen or a substituted or unsubstituted $C_1$-$C_{36}$ alkyl group; $R_4$ is hydrogen or a substituted or unsubstituted $C_1$-$C_{36}$ alkyl group; $R_5$ is hydrogen or a substituted or unsubstituted $C_1$-$C_{36}$ alkyl group; $R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is hydrogen or a substituted or unsubstituted $C_1$-$C_4$ alkyl group.

For purposes of this detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. For example, although reference is made herein to "a" halogenated compound, "an" isocyanato functional alkoxy silane, "an" imidazole, or "a" metal catalyst, a combination (i.e., a plurality) of these components can be used. In addition, in this application, the use of "or" means "and/or" unless specifically stated otherwise, even though "and/or" may be explicitly used in certain instances.

As used herein, "including," "containing" and like terms are understood in the context of this application to be synonymous with "comprising" and are therefore open-ended and do not exclude the presence of additional undescribed or unrecited elements, materials, ingredients or method steps. As used herein, "consisting of" is understood in the context of this application to exclude the presence of any unspecified element, ingredient or method step. As used herein, "consisting essentially of" is understood in the context of this application to include the specified elements, materials, ingredients or method steps "and those that do not materially affect the basic and novel characteristic(s)" of what is being described.

Whereas specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

ASPECTS

Aspects of the invention include, but are not limited to, the following:

1. A method of preparing an alkoxy silane functional ionic liquid comprising:

reacting a halogenated compound comprising a halogen and an active hydrogen functional group, an isocyanato functional alkoxy silane, and an ionizable compound capable forming an ionic bond with the halogen to form the alkoxy silane functional ionic liquid.

2. The method of Aspect 1, wherein the method comprises:
a first step comprising reacting the halogenated compound and the isocyanato functional alkoxy silane to form a halogenated alkoxy silane, and
a second step comprising reacting the halogenated alkoxy silane with the ionizable compound to form the alkoxy silane functional ionic liquid.

3. The method of Aspect 1, wherein the method comprises:
a first step comprising reacting the halogenated compound and the ionizable compound to form an ionic liquid comprising an active hydrogen functional group, and
a second step comprising reacting the ionic liquid comprising an active hydrogen functional group with the isocyanato functional alkoxy silane to form the alkoxy silane functional ionic liquid.

4. The method of any of the preceding Aspects, wherein the halogenated compound comprises a halogenated alcohol, wherein the halogenated alcohol preferably comprises 3-chloro-propanol.

5. The method of any of the preceding Aspects, wherein the isocyanato functional alkoxy silane comprises an isocyanato functional trialkoxy silane represented by Formula (I):

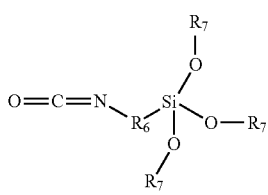

(I)

wherein $R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is a $C_1$ to $C_4$ alkyl group, wherein the isocyanato functional trialkoxy silane preferably comprises isocyanatopropyl trimethoxy silane.

6. The method of any of the preceding Aspects, wherein the ionizable compound comprises an imidazole, wherein the imidazole preferably comprises N-methyl imidazole.

7. The method of any of the preceding Aspects, wherein the reaction occurs in the presence of a metal catalyst, wherein the metal catalyst preferably comprises a tin catalyst.

8. An alkoxy silane functional ionic liquid prepared according to the method of any of the preceding Aspects.

9. The alkoxy silane functional ionic liquid of Aspect 8 represented by Formula (II):

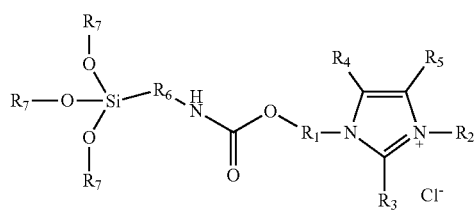

(II)

wherein $R_1$ is a substituted or unsubstituted $C_1$-$C_{36}$ alkanediyl group or a substituted or unsubstituted $C_6$-$C_{36}$ divalent aromatic group;

$R_2$ is hydrogen, a substituted or unsubstituted $C_1$-$C_{36}$ alkyl group or a substituted or unsubstituted $C_6$-$C_{36}$ aromatic group;

$R_3$ is hydrogen or a substituted or unsubstituted $C_1$-$C_{36}$ alkyl group;

$R_4$ is hydrogen or a substituted or unsubstituted $C_1$-$C_{36}$ alkyl group;

$R_5$ is hydrogen or a substituted or unsubstituted $C_1$-$C_{36}$ alkyl group;

$R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is a substituted or unsubstituted $C_1$-$C_4$ alkyl group.

10. The alkoxy silane functional ionic liquid of Aspect 8 represented by Formula (III):

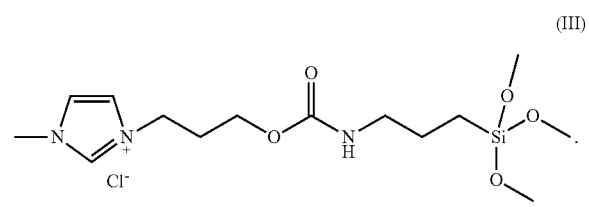

(III)

11. The alkoxy silane functional ionic liquid of Aspect 8 represented by Formula (IV):

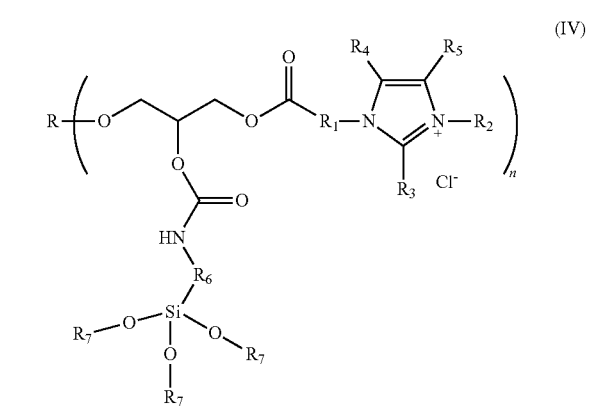

(IV)

wherein n≥1;

R is a monovalent or polyvalent, substituted or unsubstituted $C_1$-$C_{36}$ alkane group, a monovalent or polyvalent, substituted or unsubstituted $C_6$-$C_{36}$ aromatic group, or a monovalent or polyvalent, substituted or unsubstituted $C_3$-$C_{36}$ cycloaliphatic group;

$R_1$ is a substituted or unsubstituted $C_1$-$C_{36}$ alkanediyl group or a substituted or unsubstituted $C_6$-$C_{36}$ divalent aromatic group;

$R_2$ is hydrogen, a substituted or unsubstituted $C_1$-$C_{36}$ alkyl group, or a substituted or unsubstituted $C_6$-$C_{36}$ aromatic group;

$R_3$ is hydrogen or a substituted or unsubstituted $C_1$-$C_{36}$ alkyl group;

$R_4$ is hydrogen or a substituted or unsubstituted $C_1$-$C_{36}$ alkyl group;

$R_5$ is hydrogen or a substituted or unsubstituted $C_1$-$C_{36}$ alkyl group;

$R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is a substituted or unsubstituted $C_1$-$C_4$ alkyl group.

12. The alkoxy silane functional ionic liquid of Aspect 8 represented by Formula (IV):

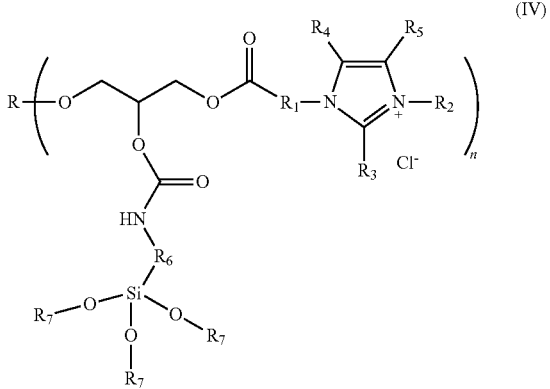

wherein n≥1;

R is a monovalent or polyvalent polyester group having a number average molecular weight ($M_n$) of greater than 200 g/mol;

$R_1$ is a substituted or unsubstituted $C_1$-$C_{36}$ alkanediyl or a substituted or unsubstituted $C_6$-$C_{36}$ divalent aromatic group;

$R_2$ is hydrogen, a substituted or unsubstituted $C_1$-$C_{36}$ alkyl group, or a substituted or unsubstituted $C_6$-$C_{36}$ aromatic group;

$R_3$ is hydrogen or a substituted or unsubstituted $C_1$-$C_{36}$ alkyl group;

$R_4$ is hydrogen or a substituted or unsubstituted $C_1$-$C_{36}$ alkyl group;

$R_5$ is hydrogen or a substituted or unsubstituted $C_1$-$C_{36}$ alkyl group;

$R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is a substituted or unsubstituted $C_1$-$C_4$ alkyl group.

13. The alkoxy silane functional ionic liquid of Aspect 8 represented by Formula (IV):

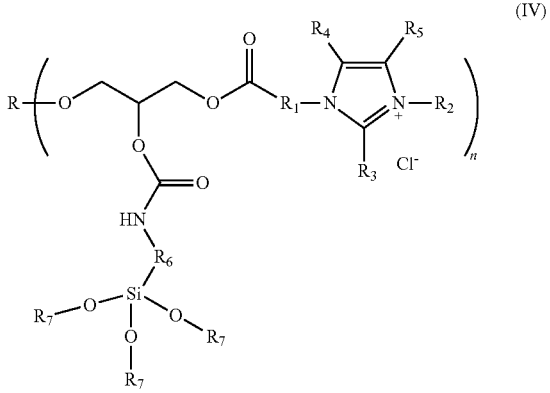

wherein n≥1;

R is a monovalent or polyvalent polyether group having a number average molecular weight ($M_n$) of greater than 200 g/mol;

$R_1$ is a substituted or unsubstituted $C_1$-$C_{36}$ alkanediyl or a substituted or unsubstituted $C_6$-$C_{36}$ divalent aromatic group;

$R_2$ is hydrogen, a substituted or unsubstituted $C_1$-$C_{36}$ alkyl group, or a substituted or unsubstituted $C_6$-$C_{36}$ aromatic group;

$R_3$ is hydrogen or a substituted or unsubstituted $C_1$-$C_{36}$ alkyl group;

$R_4$ is hydrogen or a substituted or unsubstituted $C_1$-$C_{36}$ alkyl group;

$R_5$ is hydrogen or a substituted or unsubstituted $C_1$-$C_{36}$ alkyl group;

$R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is a substituted or unsubstituted $C_1$-$C_4$ alkyl group.

14. The alkoxy silane functional ionic liquid of Aspect 8 represented by Formula (IV):

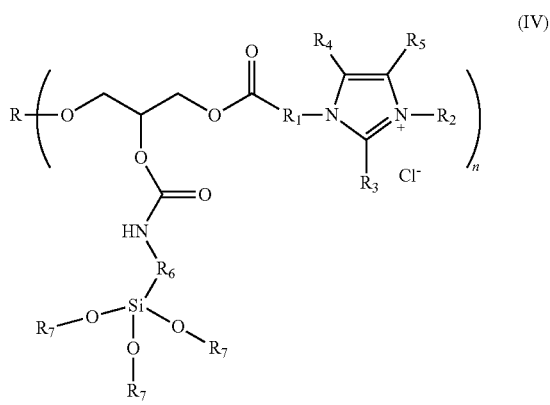

wherein n≥1;

R is a monovalent or polyvalent acrylic resin having a number average molecular weight ($M_n$) of greater than 500 g/mol;

$R_1$ is a substituted or unsubstituted $C_1$-$C_{36}$ alkanediyl or a substituted or unsubstituted $C_6$-$C_{36}$ divalent aromatic group;

$R_2$ is hydrogen, a substituted or unsubstituted $C_1$-$C_{36}$ alkyl group, or a substituted or unsubstituted $C_6$-$C_{36}$ aromatic group;

$R_3$ is hydrogen or a substituted or unsubstituted $C_1$-$C_{36}$ alkyl group;

$R_4$ is hydrogen or a substituted or unsubstituted $C_1$-$C_{36}$ alkyl group;

$R_5$ is hydrogen or a substituted or unsubstituted $C_1$-$C_{36}$ alkyl group;

$R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is a substituted or unsubstituted $C_1$-$C_4$ alkyl group.

15. The alkoxy silane functional ionic liquid of Aspect 8 represented by Formula (IV):

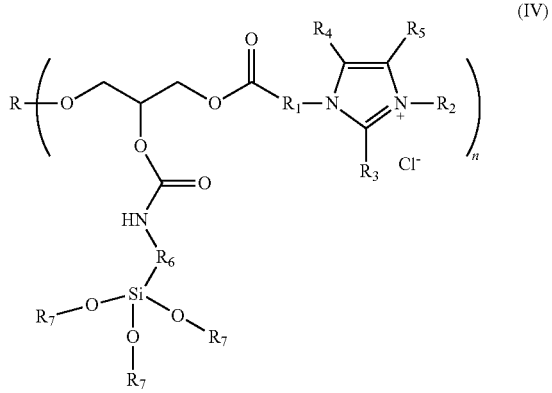

(IV)

wherein n≥1;

R is a monovalent or polyvalent polyurethane group having a number average molecular weight ($M_n$) of greater than 500 g/mol;

$R_1$ is a substituted or unsubstituted $C_1$-$C_{36}$ alkanediyl group or a substituted or unsubstituted $C_6$-$C_{36}$ divalent aromatic group;

$R_2$ is hydrogen, a substituted or unsubstituted $C_1$-$C_{36}$ alkyl group, or a substituted or unsubstituted $C_6$-$C_{36}$ aromatic group;

$R_3$ is hydrogen or a substituted or unsubstituted $C_1$-$C_{36}$ alkyl group;

$R_4$ is hydrogen or a substituted or unsubstituted $C_1$-$C_{36}$ alkyl group;

$R_5$ is hydrogen or a substituted or unsubstituted $C_1$-$C_{36}$ alkyl group;

$R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is a substituted or unsubstituted $C_1$-$C_4$ alkyl group.

Illustrating the invention are the following examples, which, however, are not to be considered as limiting the invention to their details. Unless otherwise indicated, all parts and percentages in the following examples, as well as throughout the specification, are by weight.

EXAMPLES

Example 1

Synthesis of Alkoxy Silane Functional Methylimidazolium Chloride Ionic Liquid:

Into a 500-milliliter, 4-necked kettle equipped with a stirrer, a condenser, a nitrogen inlet, and a thermocouple in a heating mantle, was charged 3-chloro-1-propanol (46.23 g, 0.489 mol, commercially available from Aldrich), toluene (110 mL) and dibutyltin dilaurate (0.028 g, commercially available from Air Product & Chemicals). Agitation by an air motor and a nitrogen flow of 0.2 scft/min through the nitrogen inlet were started. The reaction mixture was heated to 70° C. At 70° C., isocyanatopropyl trimethoxy silane (109.2 g, 0.533 mol, commercially available from Momentive) was added into reaction mixture drop wise over 30 minutes via an addition funnel. Toluene (11 mL) was then used to rinse the addition funnel. The reaction mixture was held until the isocyanate peak at 2259 $cm^{-1}$ was no longer detected by a Thermo Scientific Nicolet iS5 FT-IR Spectrometer. After the reaction was completed (approximately 3 hours), N-methyl imidazole (39.75 g, 0.484 mol, commercially available from Aldrich) was added into reaction mixture dropwise over 10 minutes. After addition, the reaction mixture was heated to reflux and held for 4 hours. The reaction mixture was then allowed to cool to 80° C. and the agitation was stopped. After 10 minutes, the reaction mixture separated into two phases. The solvent-containing phase was removed by decanting. The remaining solvent was removed by vacuum distillation. An orange oil was obtained.

Example 2

Synthesis of Hydroxyl Functional Methylimidazolium Chloride Ionic Liquid:

Into a 500-milliliter, 4-necked kettle equipped with a stirrer, a condenser, a nitrogen inlet, and a thermocouple in a heating mantle, was charged of 3-chloro-1-propanol (48.06 g, 0.5084 mol, commercially available from Aldrich), N-methylimidazole (39.75 g, 0.4842 mol, commercially available from Aldrich), and toluene (79.50 mL). Agitation by an air motor and a nitrogen flow of 0.2 scft/min were started. The reaction mixture was heated to reflux for 5 hours. The reaction mixture was allowed to cool to 70° C. and the reaction progress was monitored using a TLC plate. Dibutyltin dilaurate (0.029 g, commercially available from Air Product & Chemicals) was then added into reaction mixture and followed by the addition of isocyanatopropyl trimethoxy silane (99.25 g, 0.384 mol, commercially available from Momentive) into reaction mixture drop wise over 30 minutes. Butyl acetate (10 mL) was then used to rinse the additional funnel. After addition, the reaction mixture was held until the isocyanate peak at 2259 $cm^{-1}$ was no longer detected by a Thermo Scientific Nicolet iS5 FT-IR Spectrometer. The reaction mixture was then allowed to cool to 40° C. and the agitation was stopped. After 10 minutes, the reaction mixture separated into two phases. The solvent-containing phase was removed by decanting. The remaining solvent was removed by vacuum distillation. An orange oil was obtained.

Example 3

Synthesis of Polymeric Alkoxysilane Functional Ionic Liquid:

Into a 500-milliliter, 4-necked kettle equipped with a stirrer, a condenser, a nitrogen inlet, and a thermocouple in a heating mantle, was charged Eponex™ 1510 (115.10 g, bisphenol A-type epoxy-resin commercially available from Hexion Specialty Chemicals), toluene (107.20 mL), 2-chloroacetic acid (45.77 g, commercially available from Sigma Aldrich), and ethyltriphenylphosphonium iodide (ETPPI, 0.20 g, commercially available from Dow Chemical Co). Agitation by an air motor and a nitrogen flow of 0.2 scft/min through the nitrogen inlet were started. The reaction mixture was gradually heated to 130° C. The reaction was held at 130° C. for 13 hours until the acid value was less than 2. The acid value was determined by titration using a Metrohm 888 Titrando and 0.1 N KOH solution in methanol as the titration reagent. The reaction mixture was then cooled to 70° C. When the reaction temperature reached 70° C., dibutyltin dilaurate (0.046 g, commercially available from Air Products & Chemicals) was added to the reaction mixture. Isocyanatopropyl trimethoxy silane (99.25 grams, commercially available from Momentive) was then added into reaction mixture drop wise over 30 minutes through an addition funnel. Toluene (10 mL) was then used to rinse the addition funnel. The reaction mixture was held at 70° C. for 6 hours and the isocyanate equivalent weight was determined by reacting a sample of the isocyanate with a known excess of dibutylamine in N-methyl-2-pyrrolidone and determining the excess dibutylamine by potentiometric titration using a Metrohm 888 Titrando and 0.2N hydrochloric acid in isopropanol. The isocyanate equivalent weight was determined to be 3,038 g/eq. After calculation based on isocyanate equivalent, chloropropanol (8.0 g, commercially available from Sigma-Aldrich) was added to the reaction mixture. The reaction mixture was held until the isocyanate peak at 2259 cm$^{-1}$ was no longer detected by a Thermo Scientific Nicolet iS5 FT-IR Spectrometer. After the reaction was completed (approximately 1 hour), N-methyl imidazole (39.75 g, 0.484 mol, commercially available from Aldrich) was added into the reaction mixture dropwise over 10 minutes. After addition, the reaction mixture was heated to reflux and held for 5 hours. After holding, the reaction mixture was then allowed to cool to 80° C. and the agitation was stopped. After 10 minutes, the reaction mixture separated into two phases. The solvent-containing phase was removed by decanting. The remaining solvent was removed by vacuum distillation. An orange oil was obtained.

It will be appreciated by skilled artisans that numerous modifications and variations are possible in light of the above disclosure without departing from the broad inventive concepts described and exemplified herein. Accordingly, it is therefore to be understood that the foregoing disclosure is merely illustrative of various exemplary aspects of this application and that numerous modifications and variations can be readily made by skilled artisans which are within the spirit and scope of this application and the accompanying claims.

We claim:

1. A method of preparing an alkoxy silane functional ionic liquid comprising:
   reacting a halogenated compound comprising a halogen and an active hydrogen functional group, an isocyanato functional alkoxy silane, and an ionizable compound capable of forming an ionic bond with the halogen to form the alkoxy silane functional ionic liquid; wherein the ionizable compound comprises a heteroatom.

2. The method of claim 1, wherein the method comprises:
   a first step comprising reacting the halogenated compound and the isocyanato functional alkoxy silane to form a halogenated alkoxy silane, and
   a second step comprising reacting the halogenated alkoxy silane with the ionizable compound to form the alkoxy silane functional ionic liquid.

3. The method of claim 1, wherein the method comprises:
   a first step comprising reacting the halogenated compound and the ionizable compound to form an ionic liquid comprising an active hydrogen functional group, and
   a second step comprising reacting the ionic liquid comprising an active hydrogen functional group with the isocyanato functional alkoxy silane to form the alkoxy silane functional ionic liquid.

4. The method of claim 1, wherein the halogenated compound comprises a halogenated alcohol.

5. The method of claim 4, wherein the halogenated alcohol comprises 3-chloro-propanol.

6. The method of claim 1, wherein the isocyanato functional alkoxy silane comprises an isocyanato functional trialkoxy silane represented by Formula (I):

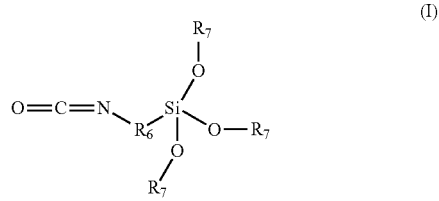

wherein $R_6$ is a $C_1$ to $C_{36}$ alkanediyl group, a linear or branched $C_3$ to $C_{36}$ cycloaliphatic group, or a linear or branched $C_6$ to $C_{36}$ aromatic group; and $R_7$ is a $C_1$ to $C_4$ alkyl group.

7. The method of claim 6, wherein the isocyanato functional trialkoxy silane comprises isocyanatopropyl trimethoxy silane.

8. The method of claim 1, wherein the ionizable compound comprises an imidazole.

9. The method of claim 8, wherein the imidazole comprises N-methyl imidazole.

10. The method of claim 1, wherein the reaction occurs in the presence of a metal catalyst.

11. The method of claim 10, wherein the metal catalyst comprises a tin catalyst.

* * * * *